US00PP31576P2

(12) United States Plant Patent
Olesen

(10) Patent No.: US PP31,576 P2
(45) Date of Patent: Mar. 24, 2020

(54) MINIATURE ROSE PLANT NAMED 'POULPAR096'

(50) Latin Name: ***Rosa* hybrid**
Varietal Denomination: Poulpar096

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/999,581

(22) Filed: Sep. 4, 2018

(51) Int. Cl.
*A01H 5/02* (2018.01)
*A01H 6/74* (2018.01)

(52) U.S. Cl.
USPC ..... Plt./121
CPC ..... *A01H 6/749* (2018.05)

(58) Field of Classification Search
USPC ..... Plt./121
See application file for complete search history.

(56) References Cited

PUBLICATIONS

Perfection by Poulsen, Novelties 2013/2014, downloaded from www.poulsenroser.dk/media/116439/Introductions-seg-3-42013-2014GBP.pdf, downloaded on Jun. 6, 2019.*
UPOV hit on miniature rose plant named 'Poulpar096', QZ PBR 20172261, filed Sep. 19, 2017.*

* cited by examiner

*Primary Examiner* — Anne Marie Grunberg

(57) ABSTRACT

A new garden rose plant of the miniature class which has abundant, deep pink flowers and attractive foliage. This new and distinct variety has shown to be uniform and stable in the resulting generations from asexual propagation.

1 Drawing Sheet

Botanical designation: *Rosa* hybrid.
Variety denomination: 'Poulpar096'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2009 and the resulting seeds were planted in a controlled environment in Fredensborg, Denmark. The new variety, named 'Poulpar096', originated as a single seedling from the stated cross.

The new variety may be distinguished from its male pollen parent and female seed parent primarily by the following characteristics. The male pollen parent plant has orange red flowers while the new variety has deep pink flowers. The female seed parent plant has a growth height of 35 to 40 cm, while the new variety grows to 30 cm.

The objective of the hybridization of this rose variety was to create a new and distinct variety with unique qualities, such as:

1. Uniform and abundant deep pink flowers;
2. Vigorous, but compact growth when propagated on its own roots;
3. Exceptional disease resistance.

This combination of qualities is not present in previously available commercial cultivars of this type, known to the inventor, and distinguish 'Poulpar096' from all other varieties of which we are aware.

As part of the rose development program, Mogens N. Olesen germinated the seeds from the aforementioned hybridization during winter of 2009 and conducted evaluations on the resulting seedlings in a controlled environment in Fredensborg, Denmark. 'Poulpar096' was selected in the spring of 2010 by the inventor as a single plant from the progeny of the aforementioned hybridization.

Asexual reproduction of 'Poulpar096' by rooted cuttings was first done by Mogens N. Olesen in the nursery in Fredensborg, Denmark in July, 2010. This initial and other subsequent asexual propagations conducted in controlled environments have demonstrated that the characteristics of 'Poulpar096' are true to type and are transmitted from one generation to the next.

DESCRIPTION OF THE DRAWING

The accompanying color illustration shows, as true as is reasonably possible to obtain in color photographs of this type, the typical characteristics of the buds, flowers, leaves, and stems, of 'Poulpar096'. Specifically illustrated in the drawing are an open flower, flower petals detached, flower bud closed and as the sepals begin to divide, sepals detached showing reproductive flower parts, leaves, and a bare stem exhibiting prickles. Plants shown are 12 months of age.

DETAILED DESCRIPTION OF THE VARIETY

The following is a description of 'Poulpar096', as observed in its growth in a container nursery in Odense Denmark. Observed plants are 12 months of age, and were grown on their own roots. Color references are made using The Royal Horticultural Society (London, England) Colour Chart, 2001, except where common terms of color are used.

For a comparison, several physical characteristics of the rose variety 'Poulesta', U.S. Plant Pat. No. 11,509, are compared to 'Poulpar096' in Chart 1.

CHART 1

| | 'Poulpar096' | 'Poulesta' |
|---|---|---|
| Petal Count | 25 | 55-65 |
| Flower Diameter | 60 mm | 40 mm |
| General Tonality of Flower Color | Red-Purple Group 57D | Red-Purple Group 63A |

FLOWER AND FLOWER BUD

Blooming habit: Continuous.

Flower bud:

*Size.*—Upon opening, 25 mm in length from base of receptacle to end of bud. Bud diameter is 8 mm.

*Bud form.*—Ovoid, somewhat lanceolate.

*Bud color.*—As sepals divide petals are Red- Purple Group N57B.

*Sepal inner surface.*—Color: Green Group 138C. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have strong foliaceous appendages on three of the five sepals.

*Sepal size.*—20 to 25 mm long, and 4 to 6 mm wide.

*Receptacle.*—Texture: Smooth. Size: 5 mm in height, 5 mm wide. Color: Yellow-Green Group 144A. Shape: Funnel.

*Pedicel.*—Surface: Rough with small prickles. Length: 20 to 40 mm. Diameter: 2 mm on average. Color: Yellow-Green Group 144B. Strength: Moderate.

*Peduncle.*—Length: 3 to 16 cm. Diameter: About 3 mm. Color: Yellow-Green Group 146A. Texture: Rough with small and large prickles.

Flower bud development: Flower buds are borne singly and in clusters of 5 to 7 flower buds per stem.

Flower bloom:

*Fragrance.*—None.

*Duration.*—The blooms have a duration on the plant of approximately 10 days. Petals fall cleanly away from plant after flowers have fully matured.

*Size.*—Flower diameter is 60 mm when open. Flower depth is 20 mm.

*Flower shape.*—Open cup, semi-double flower, with petals that curve out from the center.

*Shape of flower, side view.*—The upper portion is flat. The lower portion is concave.

Petalage: Under normal conditions, flowers have about 25 petals.

General tonality of flower: Open flowers are Red-Purple Group 57D.

Petal color:

*Upon opening, petals.*—Upper surface: Red-Purple Group 57C with a petal spot of Yellow Group 4A. Lower surface: Red-Purple Group 57C with a petal spot of Yellow Group 4B. After opening, there is no change in tonality of petals.

Petals:

*Petal reflex.*—Inner petals reflex lightly, outer petals reflex moderately to strong.

*Margin.*—Entire, uniform, with no undulations.

*Shape.*—Broad and elliptic. Apex shape: Rounded. Base shape: Acute.

*Size.*—25 mm (l)×25 mm (w).

*Texture.*—Smooth.

*Thickness.*—Average.

Petaloids:

*Size.*—About 18 mm (l) by 13 mm (w).

*Quantity.*—About 5.

*Shape.*—Elliptical with an acute base and rounded apices.

*Color.*—The upper surface is Red-Purple Group 57C with a petal spot of Yellow Group 4A. Lower surface is Red-Purple Group 57C with a petal spot of Yellow Group 4B.

Reproductive flower parts:

*Pollen.*—None observed.

*Anthers.*—Size: 2 mm in length. Color: Yellow Group 11A. Quantity: 80 on average.

*Filaments.*—Color: Yellow Group 12A. Length: 5 mm.

*Pistils.*—Length: 3 mm. Quantity: 20 on average.

*Stigmas.*—Color: Yellow-Green Group 144D.

*Styles.*—Color: Yellow-Green Group 144D.

*Location of stigmas.*—Inferior in location relative to the length of the filaments and the height of the anthers.

*Hips.*—None Observed.

PLANT

Plant growth: Upright and bushy. Plants are 30 cm in height, and 30 cm wide.

Stems:

*Color of juvenile growth.*—Yellow-Green Group 144B.

*Color of mature growth.*—Yellow-Green Group 146A.

*Length.*—Canes are about 25 cm from the base of the plant to the flowering portion.

*Diameter.*—About 3 to 4 mm.

*Internodes.*—5 to 30 mm in length.

*Surface texture.*—Young wood: Smooth. Older wood: Smooth.

Long prickles:

*Incidence.*—10 prickles per 10 cm of stem.

*Size.*—Average length of prickles on mature stems is 7 mm.

*Shape.*—Upper portion is linear. Lower portion is concave.

*Color.*—Juvenile prickles: Yellow-Green Group 145A. Mature prickles: Yellow-Green Group 145B.

Plant foliage:

*Compound leaf.*—About 85 mm (l)×60 (w).

*Quantity.*—4 to 6 leaves per 10 cm of stem.

*Leaf bearing angle to the stem.*—45 degrees.

*Color of juvenile foliage.*—Upper side: Yellow-Green Group 144A. Lower side: Yellow-Green Group 144A.

*Color of mature foliage.*—Upper side: Yellow-Green Group 147A. Lower side: Green Group 138B.

Plant leaves and leaflets:

*Stipules.*—Size: 10 mm long, mm wide. Quantity: 2 per compound leaf. Shape: Linear, slightly broad based with outward extending apices. Margins: Finely serrated. Color: Yellow-Green Group 147A.

*Petiole*.—Length: 7 to 15 mm. Diameter: 2 mm. Upper surface color: Yellow-Green Group 147B. Lower surface color: Yellow-Green Group 144A.

*Rachis*.—Length: 8 to 12 mm. Upper surface color: Yellow-Green Group 147B. Lower surface color: Yellow-Green Group 144A.

*Leaflet*.—Quantity: 5 to 7 leaflets. Margins: Serrated. Size: Terminal leaflets are about 35 to 45 mm long, 15 to 20 mm wide. Shape: Generally elliptical. Base: Rounded. Apex: Acuminate. Texture: Smooth. Thickness: Average. Arrangement: Odd pinnate. Venation: Reticulate. Glossiness: Not glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant of the miniature rose class named 'Poulpar096', substantially as illustrated and described herein, due to its abundant deep pink flowers, disease resistance, and extended period of bloom.

* * * * *

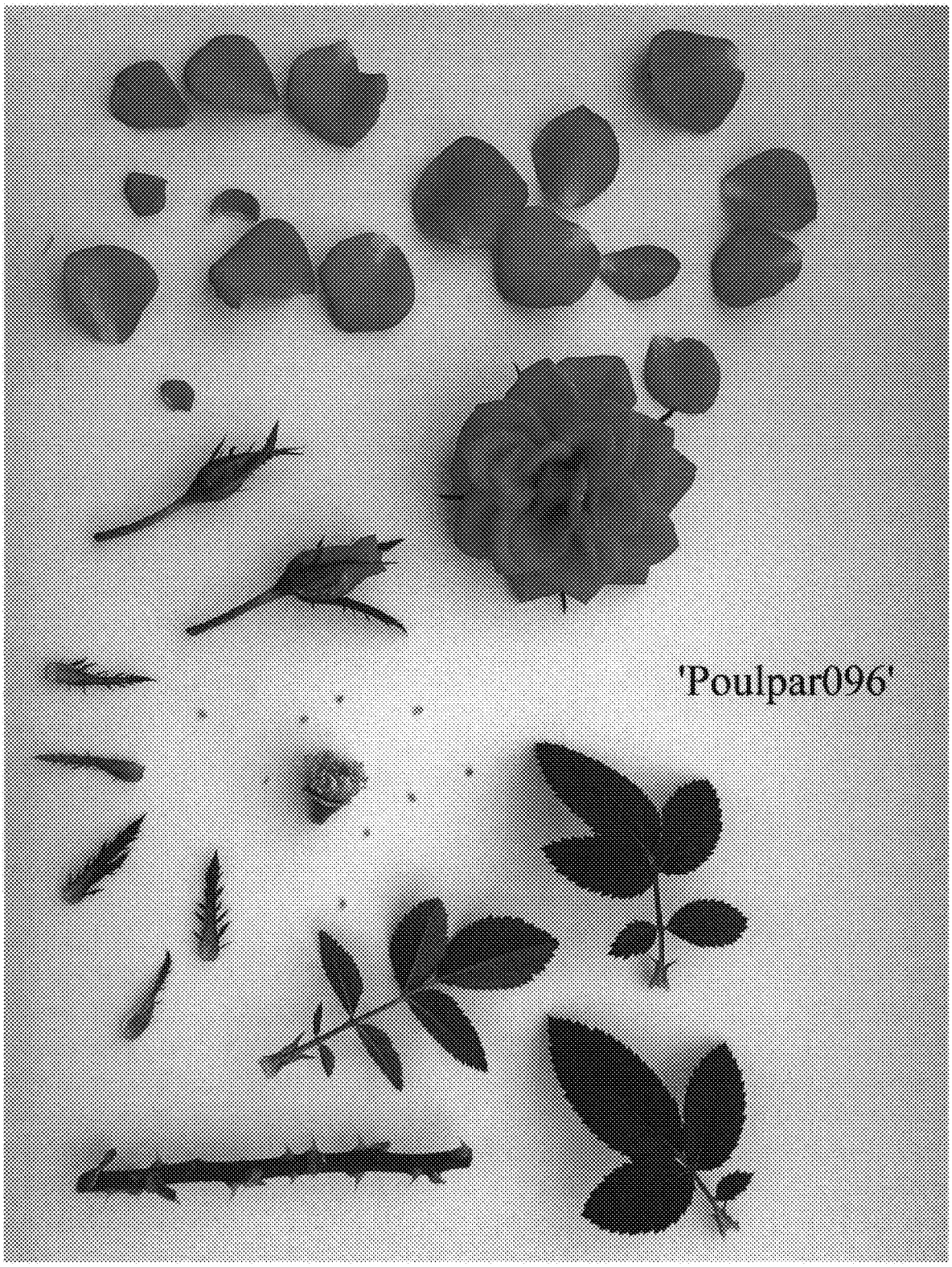
'Poulpar096'